United States Patent [19]
Allison et al.

[11] Patent Number: 5,376,369
[45] Date of Patent: Dec. 27, 1994

[54] VACCINE ADJUVANT

[75] Inventors: Anthony C. Allison, Belmont; Noelene E. Byars, Sunnyvale; Cherng-Chyi Fu, Saratoga; Deborah M. Lidgate, Los Altos; Philip L. Felgner, Rancho Santa Fe; Linda C. Foster, Sunnyvale; William A. Lee, Los Altos, all of Calif.

[73] Assignee: Syntex (U.S.A.) Inc., Palo Alto, Calif.

[21] Appl. No.: 477,281

[22] Filed: Feb. 8, 1990

Related U.S. Application Data

[63] Continuation-in-part of Ser. No. 265,868, Nov. 2, 1988, abandoned, which is a continuation-in-part of Ser. No. 116,425, Nov. 3, 1987, abandoned.

[51] Int. Cl.$^5$ ............................................. A61K 39/39
[52] U.S. Cl. .................................. 424/88; 424/279.1; 424/283.1; 514/8; 514/885; 530/322; 530/806; 530/815; 436/543
[58] Field of Search ................. 530/322, 806, 815; 424/86–92; 514/8, 885; 436/543

[56] References Cited

U.S. PATENT DOCUMENTS

| | | | |
|---|---|---|---|
| 4,082,736 | 4/1978 | Jones et al. | 424/88 |
| 4,606,918 | 8/1986 | Allison et al. | 424/88 |
| 4,770,874 | 9/1988 | Allison et al. | 424/88 |
| 4,772,466 | 9/1988 | Allison et al. | 424/88 |

OTHER PUBLICATIONS

"Formulation of Vaccine Adjuvant Muramyldipeptides. 3. Processing Optimization Characterization, and Bioactivity of an Emulsion Vehicle", Pharmaceutical Research (1989), No. 9, vol. 6, pp. 748–752.
Snippe, H., et al., *Int. Archs. Allergy appl. Immuno*, 1981, vol. 65, pp. 390–398.
Hunter, R., et al., *The Journal of Immunology*, 1981, vol. 127, No. 3, pp. 1244–1250.
Arnold, B., et al., *Eur. J. Immunol.*, 1979, vol. 9, pp. 363–366.
Ellouz, F., et al., *Biochem. & Biophys. Res. Comm.*, 1974, vol. 59, No. 4, pp. 1317–1325.
Ligate, D., et al., *Pharmaceutical Research*, 1989, vol. 6, No. 9, pp. 748–752.

*Primary Examiner*—Lester L. Lee
*Attorney, Agent, or Firm*—Carol J. Roth

[57] ABSTRACT

This invention is directed to an adjuvant composition in the form of an emulsion which is comprised of an emulsion-forming amount of a non-toxic tetra-polyol or of a POP-POE block polymer and an immunopotentiating amount of a muramyldipeptide of the formula:

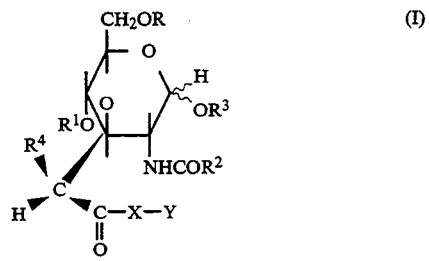

or a pharmaceutically acceptable salt thereof, where R and $R_1$ are each independently H or acyl of 1 to 22 carbon atoms, $R_2$ is optionally substituted alkyl or optionally substituted aryl, $R_3$ is H, alkyl, or aryl, $R_4$ is H or lower alkyl, X is L-alanyl, L-α-aminobutyryl, L-arginyl, L-asparginyl, L-aspartyl, L-cysteinyl, L-glutaminyl, L-glutamyl, glycyl, L-histidyl, L-hydroxyprolyl, L-isoleucyl, L-leucyl, L-lysyl, L-methionyl, L-ornithinyl, L-phenylalanyl, L-prolyl, L-seryl, L-threonyl, L-tyrosyl, L-tryptophanyl, or L-valyl, and Y is D-glutamine, D-isoglutamine or D-isoasparagine. This invention is also directed to a vaccine containing an antigen and an adjuvant composition of the invention. This invention is also directed to a process of preparing an adjuvant composition and a vaccine of the invention. This invention is also directed to a kit for extemporaneous preparation of an adjuvant composition and a vaccine of the invention.

27 Claims, No Drawings

VACCINE ADJUVANT

This is a continuation-in-part of our co-pending U.S. Ser. No. 265,868, filed Nov. 2, 1988 and now abandoned, which is a continuation-in-part of our co-pending U.S. Ser. No. 116,425, filed Nov. 3, 1987 and now abandoned, which are both incorporated herein in their entirety by reference.

BACKGROUND OF THE INVENTION

1. Field of the Invention

This invention relates to improved vaccine adjuvant compositions, improved processes for preparing said adjuvant compositions, and methods of using the improved compositions.

2. Related Disclosures

Adjuvants are useful for improving the immune response obtained with any particular antigen in a vaccine. Although some antigens are administered in vaccines without an adjuvant, there are many antigens that lack sufficient immunogenicity to stimulate an useful immune response in the absence of an effective adjuvant. Adjuvants also improve the immune response obtained from "self-sufficient" antigens, in that the immune response obtained may be increased or the amount of antigen administered may be reduced.

The standard adjuvant for use in laboratory animals is Freund's adjuvant. Freund's complete adjuvant (FCA) is an emulsion containing mineral oil and killed mycobacteria in saline. Freund's incomplete adjuvant (FIA) omits the mycobacteria. Both FIA and FCA induce exceptional humoral (antibody) immunity, and FCA additionally induces high levels of cell-mediated immunity. However, neither FIA nor FCA are acceptable for use outside the laboratory due to the adjuvants' side effects. Mineral oil is known to cause abscesses and granulomas, while *Mycobacterium tuberculosis* is the agent responsible for tuberculosis.

A number of naturally occurring compounds such as the lipid-A portion of gram negative bacteria endotoxin and trehalose dimycolate of mycobacteria have been tried as substitutes for FCA and FIA. Also, the phospholipid lysolecithin has been shown to have adjuvant activity (B. Arnold et al., *Eur. J. Immunol.*, 9:363–366 (1979)). In addition, several synthetic surfactants, for example, dimethyldioctadecyl ammonium bromide (DDA) and certain linear polyoxypropylene-polyoxyethylene (POP-POE) block polymers (available commercially under the trademark Pluronic®) have been reported as having adjuvant activity (H. Snippe et al, *Int. Archs. Allergy Appl. Immun.*, 65, 390–398 (1981)). R. Hunter et al. have reported in *J. Immunol.*, 127, 1244–1250 (1981) that POP-POE block polymers increase antibody formation to bovine serum albumin (BSA) in mice when used as the surfactant component of an mineral oil/water emulsion adjuvant formulation. While these natural and synthetic surfactants demonstrate some degree of adjuvanticity, they for the most part fail to achieve the degree of immunopotentiation obtained using FCA or FIA.

Taking another approach, it has been determined that the adjuvant effect from mycobacteria is due to a muramyl-peptide in the cell wall. The smallest fragment of this molecule that retains adjuvant activity is N-acetylmuramyl-L-alanyl-D-isoglutamine, commonly known as muramyl dipeptide or "MDP" (Ellouz et al, *Biochem. & Biophys. Res. Comm.*, Vol 59, 4, 1317 (1974)). Numerous derivatives of MDP have been prepared, and are also referred to as "MDPs." See for example Audibert et al., U.S. Pat. No. 4,158,052; Audibert et al., U.S. Pat. No. 4,220,637; Audibert et al., U.S. Pat. No. 4,323,559; Baschang et al., U.S. Pat. No. 4,323,560; Baschang et al., U.S. Pat. No. 4,409,209; Baschang et al., U.S. Pat. No. 4,423,038; Derrien et al., U.S. Pat. No. 4,185,089; Hartmann et al., U.S. Pat. No. 4,406,889; Jones et al., U.S. Pat. No. 4,082,735; Jones et al., U.S. Pat. No. 4,082,736; Le Francier et al., U.S. Pat. No. 4,427,659; Le Francier et al., U.S. Pat. No. 4,461,761; Yamamura et al., U.S. Pat. No. 4,314,998; Yamamura et al., U.S. Pat. No. 4,101,536; and Yamamura et al., U.S. Pat. No. 4,369,178, all of which are incorporated herein by reference. While these compounds are weakly effective at stimulating the immune system when administered in aqueous solution, the results generally fall short of the specific immune response obtained with FIA or FCA.

A particularly effective adjuvant composition comprising a glycopeptide, a non-toxic POP-POE block polymer, a glycol ether-based surfactant, a metabolizable oil, and buffered saline was recently described by Allison et al., U.S. Pat. Nos. 4,606,918, 4,770,874, and 4,772,466, all of which are incorporated herein by reference. The adjuvant composition described by Allison et al. is capable of inducing strong humoral and cell-mediated immune responses, equivalent or superior to the results achieved in laboratory animals using FCA. However, the composition is prone to instability and separation (e.g., creaming) upon standing. We have discovered that upon refrigeration it loses its ability to potentiate the primary response to antigens. Also, it has been found difficult to prepare a stable, homogenous emulsion with retention of full adjuvant activity on a commercial scale.

We have now discovered that an immunopotentiating glycopeptide can be formulated with a non-toxic N,N,N',N'-tetra(polyoxypropylene-polyoxyethylene)-1,2-diaminoethane block polymer ("tetra-polyol"), resulting in an adjuvant composition that overcomes certain problems of the prior art, for example, toxicity and failure to stimulate cell-mediated immunity. This new adjuvant composition has activity equal or greater than the activity of FCA and Allison's composition. The composition of the present invention is easily manufactured with full retention of activity, and displays greater pH stability than Allison's composition. Because the tetra-polyol is non-toxic, this adjuvant composition may be safely used as a vehicle for enhancing the immunogenicity of antigens administered to birds and mammals.

We have also invented a particularly advantageous method for preparing an emulsion of an adjuvant composition, using either POP-POE block polymers or tetra-polyols, which maintains the composition's efficacy, enhances its physical stability, and reduces its sensitivity to refrigeration. Remarkably, such an emulsion may even be frozen and still retain efficacy.

SUMMARY OF THE INVENTION

One aspect of the invention is an adjuvant composition in the form of an emulsion having oily particles dispersed in a continuous aqueous phase, for potentiating the immunogenicity of an antigen, which adjuvant composition comprises an emulsion-forming amount of a non-toxic tetra-polyol; optionally, an emulsion-forming amount of a non-toxic metabolizable oil; optionally, an emulsion-stabilizing amount of a glycol ether-based surfactant; water or aqueous solution; and an immunopotentiating amount of a muramyldipeptide, preferably a derivative of formula (I)

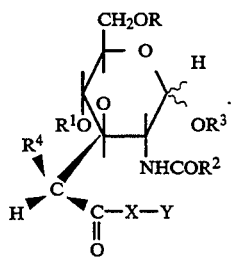

or a pharmaceutically acceptable salt thereof, wherein R and $R_1$ are each independently H or acyl of 1 to 22 carbon atoms, $R_2$ is alkyl or aryl, optionally substituted with halo, nitro, or lower alkyl, $R_3$ is H, alkyl, or aryl, $R_4$ is H or lower alkyl, X is L-alanyl, L-α-aminobutyryl, L-arginyl, L-asparginyl, L-aspartyl, L-cysteinyl, L-glutaminyl, L-glutamyl, glycyl, L-histidyl, L-hydroxyprolyl, L-isoleucyl, L-leucyl, L-lysyl, L-methionyl, L-ornithinyl, L-phenylalanyl, L-prolyl, L-seryl, L-threonyl, L-tyrosyl, L-tryptophanyl, or L-valyl, and Y is D-glutamine, D-isoglutamine or D-isoasparagine.

Another aspect of the invention is an adjuvant composition of the type mentioned above, where an emulsion-forming amount of a non-toxic POP-POE block polymer may be substituted for the tetra-polyol, and where substantially all of the volume of oily particles in the adjuvant composition is present in particles having a diameter less than about 800 nm, preferably less than 300 nm.

Another aspect of the invention is an adjuvant composition in the form of an emulsion having oily particles dispersed in a continuous aqueous phase, for potentiating the immunogenicity of an antigen, which adjuvant composition comprises an emulsion-forming amount of a non-toxic POP-POE block polymer, an emulsion-forming amount of a non-toxic metabolizable oil; an emulsion-stabilizing amount of a glycol ether-based surfactant; and water or aqueous solution, and where substantially all of the volume of oily particles in said adjuvant composition is present in particles having a diameter less than about 800 nm, preferably less than 300 nm.

Another aspect of the invention is a vaccine, comprising an adjuvant composition of the invention in combination with an immunogenic amount of an antigen.

Another aspect of the invention is a process for preparing an adjuvant composition of the invention, which process comprises preparing a first mixture comprising the polymer; optionally, the non-toxic metabolizable oil; optionally, the glycol ether-based surfactant; and water or aqueous solution; emulsifying the mixture to produce an oil-in-water type emulsion having oily particles dispersed in a continuous aqueous phase, wherein substantially all of the volume of the oily particles in the adjuvant composition is present in particles having a diameter less than about 800 nm, preferably less than 300 nm; and combining the first mixture with a muramyldipeptide derivative of formula 1.

Another aspect of the invention is a kit for extemporaneous preparation of an adjuvant composition of the invention, which kit comprises a first container containing a first mixture as described above, and a second container containing a muramyldipeptide derivative of formula (I), preferably, N-acetylmuramyl-L-threonyl-D-isoglutamine, optionally in an aqueous solution or suspension, where the concentrations of the components in each container are selected such that combination of the contents of both containers produces an adjuvant composition of the invention.

Another aspect of the invention is a kit for the preparation of a vaccine of the invention, which differs from the adjuvant kit described above in that an immunogenic amount of an antigen is added to the second container, or present in a third container.

Another aspect of the invention is a method for inducing an immune response in an animal having an immune system, which method comprises administering a vaccine of the invention.

DETAILED DESCRIPTION OF THE INVENTION

Definitions

As used in the specification and appended claims, unless specified to the contrary, the following terms have the meaning indicated:

The term "alkyl" refers to a straight or branched radical comprised of 1 to 22 carbon atoms containing no unsaturation. Examples of alkyl are methyl, ethyl, propyl, butyl, tert-butyl, hexyl, octyl, decyl, dodecyl, eicosanyl, and the like. "Lower alkyl" refers to an alkyl radical of 1 to 7 carbon atoms, for example, methyl, ethyl, propyl, butyl, tert-butyl, hexyl, 3-methylhexyl, heptyl, and the like. "Cycloalkyl" refers to cyclopropyl, cyclobutyl, cyclopentyl, cyclohexyl, cycloheptyl, and the like.

The term "acyl" refers to radicals of the formula RCO—, where R is H or alkyl as defined above. "Lower acyl" refers to such radicals where R is H or lower alkyl. Examples of acyl include formyl, acetyl, propionyl, butyryl, pentanoyl, hexanoyl, eicosanoyl, and the like. Examples of lower acyl include formyl, acetyl, propionyl, butyryl, pentanoyl, hexanoyl, and the like.

The term "halo" as used herein refers to fluoro, chloro, bromo and iodo.

The term "alkoxy" refers to a radical of the form RO—, where R is lower alkyl or cycloalkyl as defined above.

The term "aryl" refers to aromatic radicals consisting entirely of carbon and hydrogen, containing from 6 to 12 carbon atoms. Examples of aryl groups are phenyl, naphthyl, and the like.

The term "pharmaceutically acceptable salt" refers to an acid addition salt of a subject compound which possesses the desired pharmacological activity and which is neither biologically nor otherwise undesirable. This salt is formed with an inorganic acid such as hydrochloric acid, hydrobromic acid, sulfuric acid, nitric acid or phosphoric acid; or an organic acid such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The term "animal" includes humans and all domestic and wild mammals and fowl, including, without limitation, cattle, horses, swine, sheep, goats, dogs, cats, rabbits, deer, mink, chickens, ducks, geese, turkeys, game hens, and the like.

The term "treatment" as used herein covers any treatment of a disease in a bird or mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease. (It should be noted that vaccination may effect regression of a disease where the disease persists due to ineffective antigen recognition by the subject's immune system, where the vaccine effectively presents antigen.)

The term "optionally" means that the subsequently described event or circumstances may or may not occur, and that the description includes instances where said event or circumstances occurs and instances in which it does not occur.

The term "optionally substituted" as applied to aryl radicals in the invention means that the radical may be unsubstituted or substituted with one to three halo, nitro, lower alkyl, or lower alkoxy groups. The optional substituents may be the same or different.

The term "muramyldipeptide derivative" includes compounds of formula (I):

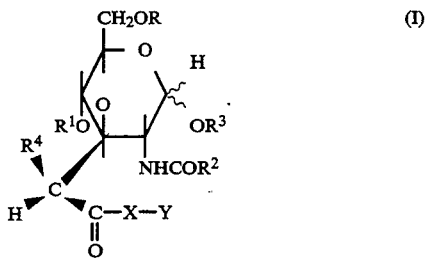

where R, R$_1$, R$_2$, R$_3$, and R$_4$ are each independently H, alkyl, acyl, or aryl optionally substituted with halo, nitro, or lower alkyl; X is one or several amino acids, and Y is D-glutamine, D-isoglutamine or D-isoasparagine, which may optionally be esterified or amidated. Preferred muramyldipeptide (MDP) derivatives are those of formula (I) wherein R and R$_1$ are H or acyl of 1 to 22 carbon atoms; R$_2$ is methyl; R$_3$ is hydrogen; X is L-alanyl, L-α-aminobutyryl, L-arginyl, L-asparginyl, L-aspartyl, L-cysteinyl, L-glutaminyl, L-glutamyl, glycyl, L-histidyl, L-hydroxyprolyl, L-isoleucyl, L-leucyl, L-lysyl, L-methionyl, L-ornithinyl, L-phenylalanyl, L-prolyl, L-seryl, L-threonyl, L-tyrosyl, L-tryptophanyl, or L-valyl, and Y is D-glutamine or D-isoglutamine. The most preferred MDP derivatives are: N-acetyl-muramyl-L-α-aminobutyryl-D-isoglutamine, 6-O-stearoyl-N-acetylmuramyl-L-α-aminobutyryl-D-isoglutamine, N-acetylmuramyl-L-threonyl-D-isoglutamine, N-acetylmuramyl-L-valyl-D-isoglutamine, N-acetylmuramyl-L-alanyl-D-isoglutamine, N-acetyldesmethylmuramyl-L-alanyl-D-isoglutamine, N-acetylmuramyl-L-alanyl-D-glutamine butyl ester (murabutide), N-acetylmuramyl-L-seryl-D-isoglutamine, and N-butyrylmuramyl-L-(α-aminobutyryl)-D-isoglutamine. Another useful MDP derivative is N-acetyl-(n-butylmuramyl)-L-α-aminobutyryl-D-isoglutamine.

The term "immunopotentiating amount" refers to the amount of MDP derivative needed to effect an increase in antibody titer and/or cell mediated immunity when administered with an antigen in a composition of the invention, as compared with the titer level observed in the absence of the MDP. As can be appreciated, each MDP may have an effective dose range that may differ from other MDPs. Thus, a single dose range cannot be prescribed which will have a precise fit for each possible muramyldipeptide within the scope of this invention. However, the immunopotentiating amount may easily be determined by one of ordinary skill in the art. As a general rule, the muramyldipeptide will preferably be present in an amount between 0.0001% and 10%. A more preferred amount is between 0.005% and 1%.

The term "non-toxic metabolizable oil" refers to an oil of 6 to 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil which can be metabolized in the body of the subject to which the adjuvant is administered, and which is not toxic to the organism. It is essential that the oil be metabolized by the animal or bird to which it is administered to avoid causing abscesses, granulomas or carcinomas. Nuts, seeds and grains are common sources of vegetable oils. Synthetic oils within the scope of this invention include "Neobee®" (available from PVO International, Inc., Chemical Specialities Division, 416 Division Street, Boongon, N.J.) and others. Shark liver oil contains a branched, unsaturated oil known as squalene, 2,6,10,15,19,23-hexamethyl-2,6,10,14,18,22-tetracosahexene which is particularly preferred herein. Squalane, the saturated analog of squalene is also a particularly preferred oil. Fish oils, including squalene and squalane, are readily available from commercial sources or may be obtained by methods known in the art.

An "emulsion-forming amount" of a non-toxic metabolizable oil is that amount which will form an emulsion in the presence of the tetra-polyol or POP-POE block polymer. The oil component of the adjuvant compositions and vaccines of the invention will usually be present in an amount between 1% and 30%, but preferably in an amount between 1% and 10%. It is most preferred to use about a 5% concentration of oil.

The term "substantially all" as applied to the volume of the oily particles in the adjuvant composition means that greater than 70% of the total volume of the oily particles, preferably greater than 80% of the total volume, and most preferably greater than 95% of the total volume, is present in particles having a diameter less than the diameter indicated.

The aqueous portion of the adjuvant compositions of the invention is preferably buffered isoosmotic saline. Because the adjuvant compositions are intended for parenteral administration, it is preferred to formulate these solutions so that the tonicity is essentially the same as normal physiological fluids in order to prevent post-administration swelling or rapid absorption of the composition due to differential ion concentrations between the composition and physiological fluids. It is also preferred to buffer the saline in order to maintain a pH compatible with normal physiological conditions. Also, in certain instances, it may be necessary to maintain the pH at a particular level in order to insure the stability of certain composition components, such as the glycopeptides. Any physiologically acceptable buffer may be used herein, but it has been found that it is most convenient to use a phosphate buffer. Any other acceptable buffer such as acetate, Tris, bicarbonate, carbonate, and the like can be used as a substitute for a phosphate buffer. It is preferred to use phosphate buffered saline, or saline buffered with a mixture of phosphate and acetate.

The term "antigen" refers to any substance, usually a protein or glycoprotein, lipoprotein, saccharide, polysaccharide or lipopolysaccharide, which upon administration stimulates the formation of specific antibodies and reacts specifically in vivo or in vitro with a homologous antibody. Moreover, it stimulates the proliferation of T-lymphocytes with receptors for the antigen, and can react with the lymphocytes to initiate the series of responses designated cell-mediated immunity.

The term "antigen" as used herein also includes combinations of haptens with a carrier. A hapten is a portion of an antigenic molecule or antigenic complex that determines its immunological specificity, but is not sufficient to stimulate an immune response in the absence of a carrier. Commonly, a hapten is a relatively small peptide or polysaccharide and may be a fragment of a naturally occurring antigen. In artificial antigens, it may be a low molecular weight substance such as, for example, an arsanilic acid derivative. A hapten will react specifically in vivo and in vitro with homologous antibodies or T-lymphocytes. Haptens are typically attached to a large carrier molecule such as bovine serum albumin (BSA) or keyhole limpet hemocyanin (KLH) by either covalent or non-covalent binding before formulation as a vaccine. For example, a common artificial antigen used to test vaccines and adjuvants consists of 2,4-dinitrophenol (DNP) covalently bound to BSA. Suitable antigens for use in this invention include antigens for hepatitis B, influenza, AIDS and herpes.

The term "immunogenic amount" of an antigen refers to an amount of antigen sufficient to stimulate a useful immune response, when administered with an adjuvant of the invention. The amount of antigen necessary to provide an immunogenic amount is readily determined by one of ordinary skill in the art, e.g., by preparing a series of vaccines of the invention with varying concentrations of antigen, administering the vaccines to suitable laboratory animals (e.g., guinea pigs), and assaying the resulting immune response by measuring serum antibody titer, antigen-induced swelling in the skin, and the like.

The term "tetra-polyol" as used herein refers to N,N,N',N'-tetra(polyoxypropylene-polyoxyethylene)-1,2-diaminoethane block polymers. These compounds may be prepared by the process disclosed in U.S. Pat. No. 2,979,528, or may be obtained commercially from BASF-Wyandotte under the trademark Tetronic ®.

Tetronic ® tetra-polyols are designated with a three or four digit number which indicates the average molecular weight of the polyoxypropylene (POP) portion and the percentage of the total molecular weight contributed by the polyoxyethylene (POE) portion of the molecule. The first one or two non-zero digits indicate the average molecular weight of the POP section, ranging from 501–1000 for Tetronic ® 304 to 6500–7000 for Tetronic ® 1501. The last digit indicates the percentage of POE in 10% increments, ranging from 10% for Tetronic ® 1501 to 80% for Tetronic ® 1508. The characteristics of these compounds are determined by the molecular weight of the POP portion and the amount of POE in the product. Preferred tetra-polyols in the practice of the invention are relatively insoluble in water at 25° C. and have low hydrophile/lipophile balance (HLB) values, for example, less than about 5.0, preferably less than about 2. Presently preferred tetra-polyols are Tetronic ® 1501, Tetronic ® 1301, Tetronic ® 1101, and Tetronic ® 1502, particularly Tetronic ® 1501 and Tetronic ® 1301, especially Tetronic ® 1501. Other appropriate tetra-polyols with the necessary properties may be prepared using the methods disclosed in U.S. Pat. No. 2,979,528, and are to be considered equivalents within the scope of this invention. For example, one could prepare a tetra-polyol with a POP molecular weight of 8,000 and a POE content of 8%.

The term "POP-POE block polymer" refers to a polymer made by the sequential addition of propylene oxide and then ethylene oxide to a low molecular weight, reactive compound, usually propylene glycol. These block polymers can be prepared by the methods set out in U.S. Pat. No. 2,674,619 issued to Lunsted, and are commercially available from BASF-Wyandotte under the trademark Plutonic ®. The characteristics of these block polymers are determined by the molecular weight of the POP nucleus and of the percentage POE in the product. The POP section imparts hydrophobic characteristics to the block polymer, while the POE section imparts hydrophilic characteristics. Preferred block polymers are determined by the same criteria used to select appropriate tetra-polyols.

Plutonic ® block polymers are designated by a letter prefix followed by a two or a three digit number. The letter prefixes (L, P, or F) refer to the physical form of each polymer, (liquid, paste, or flakeable solid). The first one or two digits is a code for the average molecular weight of the POP base, while the last digit indicates the amount of POE. For example, Pluronic ® L101 is a liquid having a polyoxypropylene base of average molecular weight 3,250, with 10% polyoxyethylene present at the ends of the molecule. The preferred block polymers are those which are liquid over a temperature range between about 15°–40° C. In addition, polymer mixtures of liquid and paste, liquid, paste and flakeable solid or liquid and flakeable solid mixtures which are liquid within the specified temperature range may have utility in this invention.

Preferred block polymers are those having a POP base ranging in molecular weight between about 2250 and 4300 and POE in an amount between about 1 and 30%. More preferred are those polymers wherein POP has a molecular weight falling between 3250 and 4000 and the POE component comprises 10–20%. The Pluronic ® block polymers L101, L121 and L122 fall within this definition. Most preferred are the block polymers wherein POP has a molecular weight of 4000 and POE in an amount of 10% or POP has a molecular weight of 3250 and POE in an amount of 10% e.g. Plutonic ® block polymers L121 and L101 respectively.

An "emulsion-forming amount" of tetra-polyol or POP-POE block polymer is that quantity which will form micelles or an emulsion. For the purposes of the invention this is an amount between 0.2% and 49% by volume. A more preferred amount is between 0.2% and 20%, and between 1% and 5% is even more preferred. A concentration of between 1% and 2.5% is presently most preferred.

The term "surfactant" refers to non-toxic surface active agents capable of stabilizing the emulsion. There are a substantial number of emulsifying and suspending agents generally used in the pharmaceutical sciences. These include naturally derived materials such as gums, vegetable protein, alginates, cellulose derivatives, phospholipids (whether natural or synthetic), and the like. Certain polymers having a hydrophilic substituent on the polymer backbone have surfactant activity, for example, povidone, polyvinyl alcohol, and glycol ether-based compounds. Compounds derived from long chain fatty acids are a third substantial group of emulsifying and suspending agents usable in this invention. Though any of the foregoing surfactants can be used so long as they are non-toxic, glycol ether-based surfactants are preferred. Preferred surfactants are non-ionic. These include polyethylene glycols (especially PEG 200, 300, 400, 600 and 900), Span ®, Arlacel ®, Tween ®, Myrj ®, Brij ® (all available from ICI America Inc., Wilmington, Del.), polyoxyethylene, polyol fatty acid esters, polyoxyethylene ether, polyoxypropylene fatty ethers, bee's wax derivatives containing polyoxyethylene, polyoxyethylene lanolin derivatives, polyoxyethylene fatty glycerides, glycerol fatty acid esters or other polyoxyethylene acid alcohol or ether derivatives of long-chain fatty acids of 12–21 carbon atoms. The presently preferred surfactant is Tween ® 80 (otherwise known as polysorbate 80 or polyoxyethylene 20 sorbitan monooleate), although it should be understood that any of the above-mentioned surfactants would be suitable after lack of toxicity is demonstrated.

An "emulsion-stabilizing amount" of a glycol ether-based surfactant is usually effected by having the surfactant present in an amount between 0.05% and 5%. An amount between 0.2% and 1% is preferred.

Preferred Embodiments

One aspect of the invention is an adjuvant composition in the form of an emulsion having oily particles dispersed in a continuous aqueous phase, for potentiating the immunogenicity of an antigen, which adjuvant comprises an emulsion-forming amount of a non-toxic tetra-polyol; optionally, an emulsion-forming amount of a non-toxic metabolizable oil; optionally, an emulsion-stabilizing amount of a glycol ether-based surfactant; water or aqueous solution; and an immunopotentiating amount of a muramyldipeptide, preferably a derivative of formula (I)

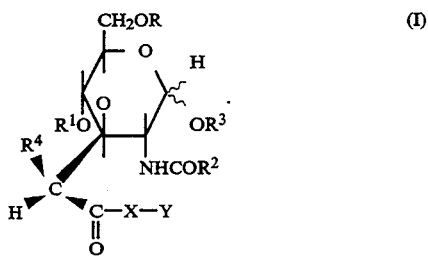

or a pharmaceutically acceptable salt thereof, wherein R and $R_1$ are each independently H or acyl of 1 to 22 carbon atoms, $R_2$ is alkyl or aryl, optionally substituted with halo, nitro, or lower alkyl, $R_3$ is H, alkyl, or aryl, $R_4$ is H or lower alkyl, X is L-alanyl, L-α-aminobutyryl, L-arginyl, L-asparginyl, L-aspartyl, L-cysteinyl, L-glutaminyl, L-glutamyl, glycyl, L-histidyl, L-hydroxyprolyl, L-isoleucyl, L-leucyl, L-lysyl, L-methionyl, L-ornithinyl, L-phenylalanyl, L-prolyl, L-seryl, L-threonyl, L-tyrosyl, L-tryptophanyl, or L-valyl, and Y is D-glutamine, D-isoglutamine or D-isoasparagine. A preferred subgenus is an adjuvant composition wherein said tetra-polyol has a polyoxypropylene base of molecular weight between 6500 and 7000 and has polyoxyethylene in an amount between 1% and 10% of said tetra-polyol, i.e., Tetronic ® 1501, particularly where said muramyldipeptide derivative of formula (I) is N-acetyl-muramyl-L-threonyl-D-isoglutamine. A preferred class of this subgenus is an adjuvant composition which includes a non-toxic metabolizable oil, especially where said oil is squalene or squalane. A preferred subclass of this class is the adjuvant composition which includes a glycol ether-based surfactant, expecially where said surfactant is Tween ® 80, particularly where said water or aqueous solution comprises isotonic buffered saline, and especially where substantially all of the volume of the oily particles in the adjuvant composition is present in particles having a diameter less than about 800 nm, preferably less than about 300 nm.

Another preferred subgenus is the adjuvant composition wherein said tetra-polyol is Tetronic ® 1501 and said muramyldipeptide derivative of formula (I) is N-acetylmuramyl-L-alanyl-D-glutamine butyl ester.

Another aspect of the invention is an adjuvant composition in the form of an emulsion having oily particles dispersed in a continuous aqueous phase, for potentiating the immunogenicity of an antigen, which adjuvant composition comprises a non-toxic tetra-polyol in an amount between 0.2% and 49%; a non-toxic metabolizable oil in an amount between 0% and 15%: a glycol ether-based surfactant in an amount between 0% and 5%; water or aqueous solution; and a muramyldipeptide derivative of formula (I) (% are vol./vol., except for the muramyldipeptide which is wt./vol.) in an amount between 0.0001% and 10%. A preferred subgenus is the adjuvant wherein said tetra-polyol has a polyoxypropylene base of molecular weight between 6500 and 7000 and has polyoxyethylene in an amount between 1% and 10% of said tetra-polyol, i.e., Tetronic ® 1501, particularly where said muramyldipeptide derivative of formula (I) is N-acetyl-muramyl-L-threonyl-D-isoglutamine. A preferred class of this subgenus is the adjuvant composition which includes a non-toxic metabolizable oil, wherein said oil is squalene or squalane. A presently preferred embodiment of the invention is the adjuvant composition in the form of an emulsion having oily particles dispersed in a continuous aqueous phase, for potentiating the immunogenicity of an antigen, which adjuvant comprises Tetronic ® 1501 in an amount between 1% and 10%; squalane or squalene in an amount between 1% and 10%; Tween ® 80 in an amount of about 0.2%; isotonic buffered saline (using phosphate buffers, acetate buffers, or combinations thereof); and N-acetylmuramyl-L-threonyl-D-isoglutamine in an amount between 0.0001% and 10%, particularly where substantially all of the volume of the oily particles in the adjuvant composition is present in particles having a diameter less than about 800 nm, preferably less than about 300 nm.

Another aspect of the invention is an adjuvant composition in the form of an emulsion having oily particles dispersed in a continuous aqueous phase, for potentiating the immunogenicity of an antigen, which adjuvant composition comprises an emulsion-forming amount of a non-toxic POP-POE block polymer; optionally, an emulsion-forming amount of a non-toxic metabolizable oil; optionally, an emulsion-stabilizing amount of a glycol ether-based surfactant; water or aqueous solution; and an immunopotentiating amount of a muramyldipeptide derivative of formula (I) or a pharmaceutically acceptable salt thereof, wherein substantially all of the volume of the oily particles in the adjuvant composition is present in particles having a diameter less than about 800 nm, preferably less than about 300 nm. A preferred subgenus is the adjuvant wherein said non-toxic POP-POE block polymer is liquid over a temperature range between about 15° C. to 40° C., has a polyoxypropylene base of molecular weight of 4000 and has polyoxyethylene in an amount of 10% of the block polymer, i.e., Pluronic® L121, particularly where said muramyldipeptide derivative of formula (I) is N-acetyl-muramyl-L-threonyl-D-isoglutamine. A preferred class of this subgenus is the adjuvant composition which includes a non-toxic metabolizable oil, particularly where said oil is is squalene or squalane. A preferred subclass of this class is the adjuvant composition which includes a glycol ether-based surfactant, especially when said surfactant is Tween® 80, and particularly where said water or aqueous solution comprises isotonic buffered saline.

Another aspect of the invention is an adjuvant composition in the form of an emulsion having oily particles dispersed in a continuous aqueous phase, for potentiating the immunogenicity of an antigen, which adjuvant comprises a non-toxic POP-POE block polymer in an amount between 0.2% and 49%; a non-toxic metabolizable oil in an amount between 0% and 15%; a glycol ether-based surfactant in an amount between 0% and 5%; water or aqueous solution; and a muramyldipeptide derivative of formula (I) or a pharmaceutically acceptable salt thereof in an amount between 0.0001% and 10%, where substantially all of the volume of the oily particles in the adjuvant composition is present in particles having a diameter less than about 800 nm, preferably less than about 300 nm, (% are vol./vol., except for the muramyldipeptide which is wt./vol.). A preferred subgenus is the adjuvant composition wherein said POP-POE block polymer is Pluronic® L121, particularly where said muramyldipeptide derivative of formula (I) is N-acetylmuramyl-L-threonyl-D-isoglutamine. A preferred class of this subgenus is the adjuvant composition which includes a non-toxic metabolizable oil, wherein said oil is squalene or squalane. A preferred subclass of this class is the adjuvant composition which includes a glycol ether-based surfactant, wherein said surfactant is Tween® 80. A presently preferred embodiment is the adjuvant composition in the form of an emulsion having oily particles dispersed in a continuous aqueous phase, for potentiating the immunogenicity of an antigen, which adjuvant composition comprises Pluronic® L121 in an amount of 1–10%; squalane or squalene in an amount of 1–10%; Tween® 80 in an amount of about 0.2%; isotonic buffered saline; and N-acetylmuramyl-L-threonyl-D-isoglutamine in an amount between 0.0001% and 10%, wherein substantially all of the volume of the oily particles in the adjuvant composition is present in particles having a diameter less than about 800 nm, preferably less than about 300 nm.

Another aspect of the invention is a vaccine comprising an adjuvant composition of the invention in combination with an immunogenic amount of an antigen. Suitably this is a vaccine in the form of an emulsion having oily particles dispersed in a continuous aqueous phase, for immunizing an animal, which vaccine comprises an immunogenic amount of an antigen; an emulsion-forming amount of a non-toxic tetra-polyol or a non-toxic POP-POE block polymer; optionally, an emulsion-forming amount of a non-toxic metabolizable oil; optionally, an emulsion-stabilizing amount of a glycol ether-based surfactant; water or aqueous solution; and an immunopotentiating amount of a muramyldipeptide, preferably a derivative of formula (I). A preferred subgenus is the vaccine which includes a tetra-polyol, especially where said tetra-polyol is Tetronic® 1501. Another preferred subgenus is the vaccine which includes a POP-POE block polymer, wherein said block polymer is Pluronic® L121. A preferred class of the subgenus is the vaccine wherein substantially all of the volume of the oily particles in the adjuvant composition is present in particles having a diameter less than about 800 nm, preferably less than about 300 nm. Another preferred class is the vaccine wherein said muramyldipeptide derivative of formula (I) is N-acetyl-muramyl-L-threonyl-D-isoglutamine. Another preferred class is the vaccine wherein said muramyldipeptide derivative of formula (I) is N-acetylmuramyl-L-alanyl-D-glutamine butyl ester. A preferred subclass of these classes is the adjuvant composition which includes a non-toxic metabolizable oil, wherein said oil is squalene or squalane. Another preferred subclass is the adjuvant which includes a glycol ether-based surfactant, wherein said surfactant is Tween® 80. A presently preferred embodiment is the vaccine which comprises Tetronic® 1501 in an amount between 1% and 10%; squalane or squalene in an amount between 1% and 10%; Tween® 80 in an amount of about 0.2%; isotonic buffered saline; and N-acetylmuramyl-L-threonyl-D-isoglutamine in an amount between 0.0001% and 10%, especially where substantially all of the volume of the oily particles in the adjuvant composition is present in particles having a diameter less than about 800 nm, preferably less than about 300 nm. Another preferred embodiment is the vaccine which comprises Pluronic® L121 in an amount between 1% and 10%; squalane or squalene in an amount between 1% and 10%; Tween® 80 in an amount of about 0.2%; isotonic buffered saline; and N-acetyl-muramyl-L-threonyl-D-isoglutamine in an amount between 0.0001% and 10%.

Another aspect of the invention is a process for preparing an adjuvant composition of the invention, which process comprises preparing a first mixture comprising a non-toxic tetra-polyol or a non-toxic POP-POE block polymer; optionally, a non-toxic metabolizable oil; optionally, a glycol ether-based surfactant; and water or aqueous solution; emulsifying said first mixture to produce an emulsion having oily particles dispersed in a continuous aqueous phase, wherein substantially all of the volume of the oily particles in the adjuvant composition is present in particles having a diameter less than about 800 nm, preferably less than about 300 nm; and combining said emulsion with a muramyldipeptide derivative of formula (I) or a pharmaceutically acceptable salt thereof. A preferred class is the process wherein said first mixture is emulsified using a Microfluidizer® (or other suitable emulsifying technique) to obtain an emulsion wherein substantially all of the volume of the oily particles in the emulsion is present in particles having a diameter less than about 800 nm, preferably less than about 300 nm. A preferred subclass of this class is the process wherein said muramyldipeptide derivative of formula (I) is combined with said emulsion in the form of an aqueous solution or suspension.

Another aspect of the invention is a process for preparing the adjuvant composition or vaccine of the invention, which process comprises mixing together the aqueous phase and the emulsion-forming amount of the non-toxic tetra-polyol or of the POP-POE block polymer so as to form an emulsion.

Another aspect of the invention is a kit for extemporaneous preparation of an adjuvant composition of the invention, which kit comprises a first container containing an emulsion having oily particles dispersed in a continuous aqueous phase, where said emulsion comprises Tetronic® 1501 or Pluronic® L121, squalane or squalene, optionally Tween® 80, and isotonic buffered saline; and a second container containing N-acetyl-muramyl-L-threonyl-D-isoglutamine in powder form (preferably lyophilized) or in aqueous solution or suspension, where the concentrations of the components in each container are selected such that combination of the contents of both containers produces an adjuvant composition comprising Tetronic® 1501 or Pluronic® L121 in an amount between 1% and 30%, squalane or squalene in an amount between 1% and 30%, Tween® 80 in an amount between 0% and 5%, N-acetylmuramyl-L-threonyl-D-isoglutamine in an amount between 0.0001% and 30%, and isotonic buffered saline. A preferred subgenus is the kit which includes Tetronic® 1501. Another preferred subgenus is the kit which includes Pluronic® L121. A preferred class of both subgenera is the kit wherein substantially all of the volume of the oily particles in the adjuvant composition is present in particles having a diameter less than about 800 nm, preferably less than about 300 nm.

Another aspect of the invention is a kit for extemporaneous preparation of an adjuvant composition of the invention, which kit comprises a first container containing the emulsion of the tetra-polyol or POP-POE polymer in the aqueous phase, and a second container containing the muramyldipeptide.

Another aspect of the invention is a kit for extemporaneous preparation of a vaccine of the invention, which kit comprises a first container containing an emulsion having oily particles dispersed in a continuous aqueous phase, where said emulsion comprises Tetronic® 1501 or Pluronic® L121, squalane or squalene, optionally Tween® 80, and isotonic buffered saline; and a second container containing N-acetylmuramyl-L-threonyl-D-isoglutamine in powder form (preferably lyophilized), or in aqueous solution or suspension, and an immunogenic amount of an antigen; where the concentrations of the components in each container are selected such that combination of the contents of both containers produces an vaccine composition comprising Tetronic® 1501 or Pluronic® L121 in an amount of 1-10%, squalane or squalene in an amount between 1% and 10%, Tween® 80 in an amount of about 0.2%, N-acetylmuramyl-L-threonyl-D-isoglutamine in an amount between 0.0001% and 10%, an immunogenic amount of an antigen, and isotonic buffered saline. Optionally, the antigen can be in a separate third container. A preferred subgenus is the kit which includes Tetronic® 1501. Another preferred subgenus is the kit which includes Plutonic® L121. A preferred class of both subgenera is the kit wherein substantially all of the volume of the oily particles in the adjuvant composition is present in particles having a diameter less than about 800 nm, preferably less than about 300 nm.

Another aspect of the invention is a kit for extemporaneous preparation of a vaccine of the invention, which kit comprises a first container containing the emulsion of the tetra-polyol or POP-POE block polymer in the aqueous phase and a second container containing the antigen, wherein the muramyldipeptide may be present in a third container, or in the first or second containers.

As noted, suitably in the kits of the invention the muramyldipeptide is present as a powder, preferably a lyophilized powder.

Another aspect of the invention is a method for inducing an immune response in an animal having an immune system, which method comprises administering a vaccine comprising an immunogenic amount of an antigen; an emulsion-forming amount of a non-toxic tetra-polyol or of a non-toxic POP-POE block polymer; optionally, an emulsion-forming amount of a non-toxic metabolizable oil; optionally, an emulsion-stabilizing amount of a glycol ether-based surfactant; water or aqueous solution; and an immunopotentiating amount of a muramyldipeptide derivative of formula (I)

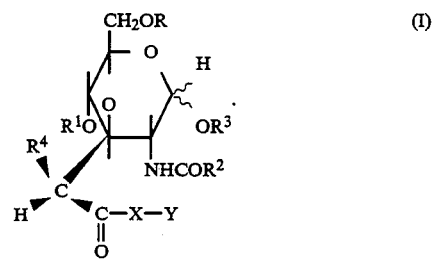

or a pharmaceutically acceptable salt thereof, wherein R and $R_1$ are each independently H or acyl of 1 to 22 carbon atoms; $R_2$ is alkyl or aryl, optionally substituted with halo, nitro, or lower alkyl; $R_3$ is H, alkyl, or aryl; $R_4$ is H or lower alkyl; X is L-alanyl, L-α-aminobutyryl, L-arginyl, L-asparginyl, L-aspartyl, L-cysteinyl, L-glutaminyl, L-glutamyl, glycyl, L-histidyl, L-hydroxyprolyl, L-isoleucyl, L-leucyl, L-lysyl, L-methionyl, L-ornithinyl, L-phenylalanyl, L-prolyl, L-seryl, L-threonyl, L-tyrosyl, L-tryptophanyl, or L-valyl; and Y is D-glutamine, D-isoglutamine or D-isoasparagine. A preferred class is the method which includes a non-toxic tetra-polyol, especially where said tetra-polyol is Tetronic® 1501. Another preferred class is method which includes a non-toxic POP-POE block polymer, especially where said polymer is Pluronic® L121. A preferred subclass is the method wherein substantially all of the volume of the oily particles in the adjuvant composition is present in particles having a diameter less than about 800 nm, preferably less than about 300 nm. A presently preferred embodiment is the method for inducing an immune response in an animal having an immune system, which method comprises administering a vaccine comprising Tetronic® 1501 in an amount between 1% and 10%; squalane or squalene in an amount between 1% and 10%; Tween® 80 in an amount of about 0.2%; isotonic buffered saline; N-acetylmuramyl-L-threonyl-D-isoglutamine in an amount between 0.0001% and 10%; and an immunogenic amount of an antigen. Another presently preferred embodiment is the method for inducing an immune response in an animal having an immune system, which method comprises administering a vaccine comprising Plutonic® L121 in an amount between 1% and 10%; squalane or squalene in an amount between 1% and 10%; Tween® 80 in an amount of about 0.2%; isotonic buffered saline; N-acetylmuramyl-L-threonyl-D-isoglutamine in an amount between 0.0001% and 10%; and an immunogenic amount of an antigen.

Preparation

The components of the adjuvant composition of the invention may be obtained through commercial sources, or may be prepared by one of ordinary skill in the art.

The tetra-polyols may be prepared by the process disclosed in U.S. Pat. No. 2,979,528, or may be obtained commercially from BASF-Wyandotte under the trademark Tetronic ®.

The POP-POE block polymers can be prepared by the methods set out in U.S. Pat. No. 2,674,619 issued to Lunsted, and are commercially available from BASF-Wyandotte under the trademark Pluronic ®.

The glycol-ether based surfactants PEG 200, 300, 400, 600 and 900, Span ®, Arlacel ®, Tween ®, Myrj ®, Brij ®, and the like are readily available commercially from ICI America Inc., Wilmington, Del., and others.

The non-toxic metabolizable oils are available from a variety of sources: e.g., squalane and squalene are available from Aldrich Chemical Co.

The muramyldipeptide derivatives of formula (I) may be obtained commercially from sources such as Sigma Chemical Co., or prepared following the processes disclosed in Audibert et al., U.S. Pat. No. 4,158,052; Audibert et al., U.S. Pat. No. 4,220,637; Audibert et al., U.S. Pat. No. 4,323,559; Baschang et al., U.S. Pat. No. 4,323,560; Baschang et al., U.S. Pat. No. 4,409,209; Baschang et al., U.S. Pat. No. 4,423,038; Derrien et al., U.S. Pat. No. 4,185,089; Hartmann et al., U.S. Pat. No. 4,406,889; Jones et al., U.S. Pat. No. 4,082,735; Jones et al., U.S. Pat. No. 4,082,736; Le Francier et al., U.S. Pat. No. 4,427,659; Le Francier et al., U.S. Pat. No. 4,461,761; Yamamura et al., U.S. Pat. No. 4,314,998; Yamamura et al., U.S. Pat. No. 4,101,536; and Yamamura et al., U.S. Pat. No. 4,369,178, all incorporated herein by reference.

Adjuvant compositions of the invention are prepared by emulsification, using a mixer. If an adjuvant composition is to be prepared on a laboratory scale using a tetra-polyol for immediate use, it may be mixed simply by hand. For example, Tween ® 80 and buffered saline are added to squalane and Tetronic ® 1501 in a test tube at 2X concentration, and the combination mixed using a vortex mixer to form an emulsion. To this is added a 2X solution of antigen and a muramyldipeptide derivative of formula (I) in buffered saline to form the completed vaccine. It is more preferred to use a high-shear mixer such as a Greerco Homogenizer Mixer to form a smoother, more homogenous emulsion.

Preferably, the emulsion of the adjuvant composition of the invention is "microfluidized" prior to adding the antigen, whether a tetra-polyol or a POP-POE block polymer is used. This is accomplished using a very high-shear mixer such as a Microfluidizer ® (commercially available through Microfluidics Corp., Newton, Mass.). Typically, with the Microfluidizer ®, 100 mL to 500 mL batches of emulsion are prepared. The emulsion is cycled through the Microfluidizer ® about 2-10 times, until the substantially all of the volume of the oily particles in the emulsion is present in particles having a diameter less than about 800 nm, preferably lees than about 300 nm, most preferably, less than about 200 nm. The Microfluidizer ® combines shear, turbulence and cavitation forces, the two fluidized streams interacting at very high velocities within an interaction chamber thus creating uniformly small emulsion particles. It should be understood that equipment other than the Microfluidizer ® may be capable of producing a satisfactory emulsion, and that the use of any device capable of producing an emulsion of sufficient stability and sufficiently small particle size is within the scope of this process. Normally, the muramyldipeptide derivative of formula (I) will be added after the emulsification step. Alternatively, the emulsion may be stored under refrigeration and/or nitrogen prior to the addition of the MDP and antigen.

The resulting emulsion may be assayed in a variety of ways well known in the art. The emulsion stability may be measured by allowing the emulsion to stand at room temperature, and under refrigeration, followed by observation for separation into phases. This assay may be accelerated by centrifuging the emulsion, e.g., for two hours at 4500 g.

Diameters of the oily particles present in the emulsion of the adjuvant composition of the invention may be determined by, for example, optical microscopy, transmission electron microscopy, and laser light-scattering techniques, preferably using laser photon correlation spectroscopy (PCS). PCS analysis may be performed using, for example, a Nicomp Model 200 laser particle sizer, with a model TC-100 computing autocorrelator.

Biological activity may be assayed using standard laboratory techniques, e.g., by vaccinating a standard laboratory animal (e.g., a guinea pig) with a standard antigen (e.g., BSA or DNP-BSA) using a test adjuvant formulation. After allowance of time for boosting the vaccination, and time for immunization to occur, the animal is challenged with the standard antigen and the results measured. The response may be quantified by any measure accepted in the art for measuring immune responses, e.g., in terms of serum antibody titer against the standard antigen (for humoral immunity) and skin test reaction (for cell-mediated immunity).

Administration

It will be apparent to one of ordinary skill in the art that the precise amounts of MDP derivative and antigen needed to produce a given effect will vary with the particular compounds and antigens, and with the size, age, and condition of the subject to be treated. Thus, it is impossible to state exactly the amounts needed. However, these amounts can easily be determined using methods known to those of ordinary skill in the art.

The adjuvant compositions and vaccines of the invention are generally administered by injection, particularly intramuscular injection, preferably into a large muscle.

In general, an initial vaccination is administered using the desired antigen and an adjuvant composition of the invention. The vaccination is "boosted" several weeks later (usually 2-6 weeks, for example, 4-6 weeks) using a vaccine of the invention with or without (preferably with) the MI)P component. Generally, 1-2 mL of a vaccine (such as are described in the Examples below) is administered to a human subject in the practice of the invention.

The following examples are presented as an aid to those of ordinary skill in the art, and are not to be considered as a limitation of the invention in any way.

EXAMPLE 1

Immunogenicity

A. Preparation of Adjuvant Compositions

Adjuvant compositions were prepared as follows for assay of biological activity. Each emulsion was prepared at 2× concentration prior to combination with a 2× solution of antigen.

Composition 1 (from Allison, U.S. Pat. No. 4,606,918): 5.0% Pluronic® L121, 10% squalane, 0.4% Tween® 80, qs phosphate buffered saline (pH 7.4); the components were added to a test tube and vortex-mixed until a milky emulsion was obtained. This composition was prepared immediately prior to administration.

Composition 2 (Composition 1 with refrigeration): 5.0% Pluronic® L121, 10% squalane, 0.4% Tween® 80, qs phosphate buffered saline (pH 7.4); the components were added to a test tube and vortex-mixed until a milky emulsion was obtained. The composition was then refrigerated at 4° C. beginning one day prior to administration.

Composition 3 (tetra-polyol composition of the invention): 5.0% Tetronic® 1501, 10% squalane, 0.4% Tween® 80, qs phosphate buffered saline (pH 7.4); the components were added to a test tube and vortex-mixed until a milky emulsion was obtained.

Composition 4 (microfluidized POP-POE adjuvant composition of the invention): 5.0% Pluronic® L121, 10% squalane, 0.4% Tween® 80, qs phosphate buffered saline (pH 7.4); the components were added to a test tube and vortex-mixed until a milky emulsion was obtained. This emulsion was then passed through a Microfluidizer® four times. This composition was refrigerated with Composition 2.

Composition 5: Phosphate buffered saline (pH 7.4).

Composition 6: Same as Composition 1.

To Compositions 1-5 was then added solid N-acetyl-muramyl-L-threonyl-D-isoglutamine (Thr-MDP) to a concentration of 500 μg/mL, to form the complete adjuvant "concentrate." The concentrate was then mixed with a 2× concentration solution of antigen (ovalbumin in saline, 1 mg/mL) to form a test vaccine.

Composition 6 did not receive any Thr-MDP prior to mixing with a 2× concentration solution of antigen (ovalbumin in saline, 1/mg mL) to form a test vaccine.

B. Bioactivity

Each test vaccine (0.2 mL) was administered to 8 female guinea pigs. At four weeks following administration, each animal was boosted with the same test vaccine (but without the Thr-MDP). Antibody titer was measured from serum samples collected at weeks 4 and 6 after initial administration. At 6 weeks, each animal received ovalbumin intradermally, and the diameter of the erythema, and the infiltration rating were determined after 24 hours, as an indication of cell-mediated immunity.

The results are reported in Tables 1a, 1b, 2a and 2b. Table 1a and Table 2a report the results for Compositions 1-4, which all contain either Pluronic® L151 or Tetronic® 1501. Table 1b and Table 2b report the results for Compositions 5 and 6. Each entry represents the mean obtained from 8 animals. Antibody titers were determined by hemagglutination. Infiltration was scored visually, on a 1-3 scale (1 being the weakest response, and 3 being a very obvious swelling at the skin test site).

TABLE 1a

| Composition | Antibody Titer Results | |
|---|---|---|
| | 4 weeks | 6 weeks |
| 1 (control POP-POE) | 2.25 ± .38 | 6.13 ± .30 |
| 2 (refrigerated POP-POE) | 1.38 ± .18 | 6.50 ± .19 |
| 3 (tetra-polyol) | 4.00 ± .38 | 8.13 ± .30 |
| 4 (refrigerated/ microfluidized POP-POE) | 2.87 ± .12 | 8.00 ± .27 |

TABLE 1b

| Composition | Antibody Titer Results | |
|---|---|---|
| | 4 weeks | 6 weeks |
| 5 (PBS with Thr-MDP) | 0.714 ± 0.286 | 3.286 ± 0.606 |
| 6 (POP-POE without Thr-MDP) | 2.143 ± 0.340 | 6.000 ± 0.436 |

TABLE 2a

| Composition | Cell-Mediated Immunity Results | |
|---|---|---|
| | Diameter (mm) | Infiltration |
| 1 (control POP-POE) | 16.06 | 1.75 |
| 2 (refrigerated POP-POE) | 13.81 | 1.31 |
| 3 (tetra-polyol) | 19.13 | 1.94 |
| 4 (refrigerated/ microfluidized POP-POE) | 13.56 | 1.50 |

TABLE 2b

| Composition | Cell-Mediated Immunity Results | |
|---|---|---|
| | Mean Diameter ± SE | |
| | 24 hr | 48 hr |
| 5 (PBS with Thr-MDP) | 4.143 ± 1.55 | 0.429 ± 0.429 |
| 6 (POP-POE without Thr-MDP) | 11.714 ± 0.89 | 3.857 ± 1.405 |

The results in Table 1a and 2a demonstrate that the tetra-polyol adjuvant compositions are significantly more effective for increasing the immunogenicity of antigens, and that the micro-fluidized POP-POE block polymer adjuvant compositions are at least as effective as control compositions while demonstrating superior storage stability. Tables 1b and 2b demonstrate the immunogenicity of compositions containing only Thr-MDP (Composition 5) and only Pluronic® L121 (Composition 6).

EXAMPLE 2

Physical Characteristics

The compositions prepared in Example 1(A) were examined for physical characteristics.

A. Separation

Each of the compositions (1-4) was centrifuged for 30 minutes at 4500 x G, then allowed to stand to separate into layers. The amount of separation that occurred was noted and estimated as the volume percentage of the total occupied by the upper layer. Compositions 1-3 separated about 10%, while Composition 4 separated less than about 1%.

B. Particle Size

Particle size distributions were analyzed by optical microscopy (Leitz Ortholux II POL-BK polarized light microscope), transmission electron microscopy (TEM, using a Hitachi model HS-8-1), and laser photon correlation spectroscopy (PCS, using a Nicomp Model 200 laser particle sizer, with a model TC-100 computing autocorrelator). Particle size distributions were determined for top layers and bottom layers separately. Samples analyzed by TEM and PCS were diluted 1:100 or greater before analysis. The results demonstrated that Compositions 1–3 exhibited particle sizes ranging from <0.1 μm to about 25 μm. Composition 4 exhibited particle sizes ranging from <0.1 μm to about 0.3 μm (300 nm).

EXAMPLE 3

(Compositions)

Exemplary adjuvant compositions were prepared as follows:

A. Tetronic®/Thr-MDP

| Tetronic ® 1501 | 2.5 g |
|---|---|
| Squalane | 5.0 g |
| Tween ® 80 | 0.2 g |
| Thr-MDP | 250.0 mg |
| Phosphate buffered saline | qs to 100.0 mL |

The Tetronic ® 1501, squalane, and Tween ® 80 are placed in an appropriate vessel with 85 mL of phosphate buffered saline (PBS) and are mixed with a mechanical mixer (Greerco Homogenizer-Mixer, model #1L-79, Greerco Corp., Hudson, N.H.) at about 4750 rpm for about 30–60 minutes. Then, the Thr-MDP (N-acetylmuramyl-L-threonyl-D-isoglutamine) and remaining 15 mL of PBS are stirred in, producing an adjuvant composition of the invention.

B. Similarly, proceeding as in paragraph A above but substituting N-acetylmuramyl-L-α-aminobutyryl-D-isoglutamine (Abu-MDP), 6-O-stearoyl-N-acetylmuramyl-L-α-aminobutyryl-D-isoglutamine (Abu-MDP stearate), N-acetylmuramyl-L-valyl-D-isoglutamine (Val-MDP), N-acetylmuramyl-L-alanyl-D-isoglutamine (MDP), N-acetyldesmethylmuramyl-L-alanyl-D-isoglutamine (desMe-MDP), N-acetylmuramyl-L-alanyl-D-glutamine butyl ester (N-acetylmuramyl-L-alanyl-D-glutamine butyl ester), n-butyrylmuramyl-L-(α-aminobutyryl)-D-isoglutamine, and N-acetylmuramyl-L-seryl-D-isoglutamine (Ser-MDP), for the Thr-MDP, the corresponding adjuvant compositions are prepared.

C. Pluronic®/Thr-MDP

| Pluronic ® L121 | 2.5 g |
|---|---|
| Squalane | 5.0 g |
| Tween ® 80 | 0.2 g |
| Thr-MDP | 250.0 mg |
| Phosphate buffered saline | qs to 100.0 mL |

The Pluronic ® L121, squalane, and Tween ® 80 are placed in an appropriate vessel with 85 mL of phosphate buffered saline (PBS) and are mixed with a mechanical mixer (e.g., Greerco Homogenizer-Mixer) at about 4750 rpm for about 5–10 minutes. Then, the Thr-MDP (N-acetylmuramyl-L-threonyl-D-isoglutamine) and remaining 15 mL of PBS are stirred in. The resulting emulsion is then processed through a Microfluidizer ® (Microfluidics Corp.) for at least 4 cycles to provide an adjuvant composition of the invention. Alternatively, the MDP is added after the microfluidization step.

D. Similarly, proceeding as in paragraph C above but substituting N-acetylmuramyl-L-α-aminobutyryl-D-isoglutamine (Abu-MDP), 6-O-stearoyl-N-acetylmuramyl-L-α-aminobutyryl-D-isoglutamine (Abu-MDP stearate), N-acetylmuramyl-L-valyl-D-isoglutamine (Val-MDP), N-acetylmuramyl-L-alanyl-D-isoglutamine (MDP), N-acetyldesmethylmuramyl-L-alanyl-D-isoglutamine (desMe-MDP), N-acetylmuramyl-L-alanyl-D-glutamine butyl ester (N-acetylmuramyl-L-alanyl-D-glutamine butyl ester), N-butyrylmuramyl-L-(α-aminobutyryl)-D-isoglutamine, and N-acetylmuramyl-L-seryl-D-isoglutamine (Ser-MDP), for the Thr-MDP, the corresponding adjuvant compositions are prepared.

E. Similarly, the adjuvant compositions prepared in paragraphs A and B above may be further improved by microfluidizing as described in paragraphs C and D to form the corresponding microfluidized Tetronic ® compositions.

F.
Tetronic ®/N-acetylmuramyl-L-alanyl-D-glutamine butyl ester;

| Tetronic ® 1501 | 2.0 g |
|---|---|
| Squalane | 6.0 g |
| Brij ® 80 | 0.3 g |
| N-acetylmuramyl-L-alanyl-D-glutamine butyl ester | 300.0 mg |
| Phosphate buffered saline | qs to 100.0 mL |

The composition is prepared as described in paragraphs A and E above.

G. Similarly, proceeding as described in paragraphs A–F above, but substituting Plutonic ® L101 or Tetronic ® 1301 for Plutonic ® L121 or Tetronic ® 1501, the corresponding adjuvant compositions are prepared.

H. Pluronic ®/Ser-MDP concentrate:

| Pluronic ® L121 | 2.5 g |
|---|---|
| Squalane | 5.0 g |
| Tween ® 80 | 0.2 g |
| Ser-MDP | 250.0 mg |
| Phosphate buffered saline | qs to 100.0 mL |

The Pluronic ® L121, squalane, and Tween ® 80 are placed in an appropriate vessel with PBS (qs to 50 mL) and are mixed with a mechanical mixer (Greerco Homogenizer-Mixer) at about 4750 rpm for about 5–10 minutes. The resulting emulsion is then processed through a Microfluidizer ® for 4 to 10 cycles to provide an emulsion concentrate. The Ser-MDP and remaining PBS are provided as a second component to form a two-component "kit" for extemporaneous preparation of the adjuvant. To use, the desired amount of antigen is added to the Ser-MDP solution, and the resulting solution is mixed vigorously with the emulsion component.

I. Similarly, proceeding as in paragraph H above but substituting the components described in paragraphs A–G above, the corresponding adjuvant kits are prepared.

J. Vaccines

Vaccines of the invention are prepared by adding an appropriate amount of antigen to any of the compositions described above. Suitable antigens include antigens for hepatitis B, influenza (for example, A or B), AIDS and herpes. The vaccine may contain more than one antigen if desired, for example, antigens for diphtheria, pertussis, and tuberculosis may be coadministered in a single composition.

For ease of preparation, a small portion of the PBS used may be withheld from the adjuvant preparation, e.g., one may prepare the adjuvants described above using 90 mL rather than 100 mL, and use the withheld PBS to dissolve/suspend the antigen(s). The antigen/PBS solution is then mixed with the (slightly) concentrated emulsion to prepare the final vaccine. Alternatively, and more preferably, an adjuvant emulsion (without MDP) of two times concentration is mixed with an antigen/MDP solution of two times concentration.

EXAMPLE 4

Comparison of Freshly Made and Frozen Emulsions

A. Preparation of Emulsions

Two times concentrated emulsions, consisting of 10% v/v squalane, 5% v/v Pluronic® L121 and 0.4% polysorbate 80 in phosphate buffered saline, were used in the test, having been prepared as for Composition 4 (Example 1). One emulsion was stored frozen for seven days before use, while the other was freshly prepared and kept at room temperature. On the day vaccines were prepared, Thr-MDP was added to the fresh and thawed emulsions. Equal volumes of 2× concentrated ovalbumin were added to the 2 lots of emulsions just before the vaccines were used to immunize groups of 8 female guinea pigs. The final concentrations of the constituents of the vaccines were: Phosphate buffered saline 92.33%; Squalane 5%; Pluronic® L121, 2.5%; Polysorbate 80, 0.17%; Thr-MDP 250 µg/ml; and Ovalbumin 1.0 mg/ml.

Guinea pigs were vaccinated on days 0 and 28 with 0.2 ml of vaccine per animal, bled on days 28 and 42, and skin tested with 10 µg of ovalbumin on day 42.

The results obtained, as shown below, show that the efficacy of the frozen material was equivalent to that of the freshly prepared emulsion.

TABLE 3

Antibody Titer Results[a]

| Group | Vehicle Preparation | 28 Days Mean Titer ± SE | 42 Days Mean Titer ± SE | Equivalent Dilution[b] |
|---|---|---|---|---|
| 1[c] | Fresh | 4.6 ± 0.2 | 9.0 ± 0.1 | 18,837 |
| 2[c] | Frozen | 5.1 ± 0.3 | 8.9 ± 0.1 | 17,830 |

[a]Titers are expressed as $log_3$ of the reciprocal of the serum dilution giving an optical density reading of 0.5 absorbance units, under the conditions of the assay.
[b]Titer expressed as the reciprocal of the mean serum dilution.
[c]There were 8 animals in both Group 1 and Group 2.

TABLE 4

Delayed Hypersensitivity Skin Reactions

| Group | No. of Animals | Vehicle Preparation | Mean Diameter (mm ± SE) 24 Hr | 48 Hr |
|---|---|---|---|---|
| 1 | 8 | Fresh | 14.3 ± 0.7 | 11.0 ± 1.7 |
| 2 | 8 | Frozen | 13.3 ± 2.3[a] | 11.4 ± 2.9[a] |

[a]Includes one animal which had no response and may not have been skin tested.

EXAMPLE 5

Hepatitis Virus Vaccine

Groups of 8 female Hartley guinea pigs were immunized subcutaneously with a vaccine consisting of Hepatitis B virus surface antigen (HBsAg) in adjuvant (prepared as for Composition 4, Example 1, without refrigeration) or adsorbed to alum (commercially available hepatitis vaccine). The HBsAg in saline and HBsAg adsorbed to alum were provided by Merck Sharpe and Dohme Research Laboratories. The vaccine formulation consisted of 92.33% PBS, 5% squalane, 2.5% Pluronic L121, 0.17% polysorbate 80, 100 µg/ml Thr-MDP, and either 1.0 µg/ml or 0.2 µg/ml of HBsAg. Each animal received 0.5 ml of vaccine at day 0 and week 4. The animals were bled at weeks 4, 6 and 15. Antibody titers were determined by ELISA techniques and were far superior for the vaccine of the invention.

TABLE 5

Anti-HBsAg Titers of Pooled Guinea Pig Sera

| Group | Vehicle | HBsAg Dose (µg) | ELISA Titer 4 Weeks | 6 Weeks | 15 Weeks |
|---|---|---|---|---|---|
| 1 | Adjuvant | 0.5 | 814 | 34092 | 16693 |
| 2 | Alum | 0.5 | 230 | 4002 | 3041 |
| 3 | Adjuvant | 0.1 | 52 | 6210 | 4719 |
| 4 | Alum | 0.1 | 34 | 1131 | 1409 |

EXAMPLE 6

Influenza Virus Vaccine

Groups of 10 or 11 6–7 week old female BALB/cJ mice were immunized subcutaneously with a vaccine consisting of influenza virus antigen in adjuvant (prepared as for Composition 4, Example 1, without refrigeration). The adjuvant formulation consisted of 2.5% Pluronic® L121, 5.0% squalane, 0.17% Tween® 80, 500 µg/ml Thr-MDP, and PBS qs. The influenza virus strains used were A/Taiwan, A/Leningrad and B/Ann Arbor. The antigen concentration is expressed in µg/mL of hemagglutinin (HA). The vaccine was diluted so that the mice received a 0.01 µg/mL of HA of each strain in 0.1 ml of the adjuvant. One group of mice was given adjuvant only. The groups of mice were immunized as follows:

1. Control—Adjuvant only
2. 0.01 µg of each strain in adjuvant
3. 0.01 µg of each strain in adjuvant Groups 1 and 2 were immunized at 0 and 3 weeks while group 3 was immunized at 0 time only.

At weeks 3, 5 and 9, 50 µl of blood was obtained from each mouse (under ether anesthesia) via the retro-orbital plexus. Sera were pooled by group. At week 13 the mice were bled out under ether anesthesia, and sera were kept individually as well as in pools.

The Table below shows the mean titers determined for sera from all groups at week 13. For the 0.01 µg dose levels, there was no significant difference in titer between the groups given one dose compared to those given 2 doses, when the anti-A/Taiwan or anti-A/Leningrad titers were measured. However, one dose induced significantly lower anti-B/Ann Arbor titers than did 2 doses. (Compare groups 2 and 3).

TABLE 6

| Group | HA Dose (μg) | Boost at 3 wks | Vehicle | Mean Titer ± SE A/Taiwan | A/Leningrad | B/Ann Arbor |
|---|---|---|---|---|---|---|
| 1 | 0 | + | Adjuvant | $<3.0 \pm 0^{b,c}$ | $<3.0 \pm 0^b$ | $<3.0 \pm 0^b$ |
| 2 | 0.01 | + | Adjuvant | $9.1 \pm 0.1$ | $8.0 \pm 0.2$ | $6.8 \pm 0.2$ |
| 3 | 0.01 | − | Adjuvant | $8.8 \pm 0.2$ | $7.8 \pm 0.3$ | $5.9 \pm 0.3$ |

$^a$Titer is log$_3$ of the reciprocal of the serum dilution giving an optical density of 0.5 absorbance units.
$^b$Lowest dilution tested was 1/27, i.e., $\frac{1}{3}^3$
$^c$Sera of 2 animals had titers of 3.1 and 3.2, while for the remaining B sera no antibody was detectable.

EXAMPLE 7

The ovalbumin vaccine of Example 4 was prepared as described in Composition 4, Example 1, but without the Tween® 80.

EXAMPLE 8

The ovalbumin vaccine of Example 4 was prepared as described in Composition 4, Example 1, but the vaccine composition contained only 1.25% Pluronic® L121.

EXAMPLE 9

Other Vaccines

The ovalbumin vaccine of Example 4 was prepared as described in Composition 4, Example 1, but using the following antigens in place of ovalbumin:
HIV (Human immunodeficiency virus)
Plasmodium yoelii peptides
Influenza viruses (A and B types)
Adenoviruses
Herpes simplex virus type 1, glycoprotein gD1
Melanoma antigens (mouse and human)
Foot and mouth disease virus
Hepatitis B virus surface antigens
Hepatitis A virus
Para-influenza 3 glycoproteins
SIV (simian immunodeficiency virus)
Shistoma mansoni cercaria
Folate hydrolase
Polio virus
Mouse idiotype antibody
Bacterial toxoids
Human tumor associated antigens
Simian retrovirus (type 1 & 2) peptides
Type D retrovirus
Parasite antigens
LHRH
Mouse IgG peptides
Brucella abortus proteins
HIV proteins
Fibroblast growth factors ($\alpha$ and $\beta$)
IL-6
Herpes simplex virus, type 2, early gene 22
Feline leukemia virus The weight of MDP in the vaccine was subject to minor variation depending on the species of animal tested. In some cases, the emulsion was not refrigerated before addition of the MDP and antigen.

EXAMPLE 10

A. Preparation of Vaccine

An ovalbumin vaccine was prepared as follows: 2.5% Tetronic® 1501, 5.0% squalane, 0.2% Tween® 80, qs phosphate buffered saline (pH 7.4) were added to a test tube and vortex-mixed until a milky emulsion was obtained. This emulsion was then passed through a Microfluidizer® four times. 250 μg/mL of solid N-acetyl-muramyl-L-threonyl-D-isoglutamine (Thr-MDP) was then added to the emulsion to form a 2× concentration emulsion of the adjuvant formulation. This formulation was then mixed with a 2× concentration solution of ovalbumin in saline to form the vaccine.

B. Bioactivity

A group of 8 female Sim:(HA) guinea pigs, 350 g to 400 g, were injected subcutaneously in the nuchal region with 0.2 mL of the vaccine. Each animal received 200 μg ovalbumin in the vaccine on Day 0, and 50 μg ovalbumin in the vaccine on Day 28. The animals were bled by cardiac puncture on Days 28 and 42, and skin tested on Day 42 with 10 μg ovalbumin, given intradermally. The diameter and induration of the skin tests were measured 24 and 42 hours later as an indication of cell-mediated immunity. The antibody titers were determined by passive hemagglutination and by ELISA. The results are reported in the Tables below. Each entry represents the mean obtained from the 8 animals. Infiltration was scored visually, on a 1 to 3 scale (1 being the weakest respose and 3 being a very obvious swelling at the skin test site.)

TABLE 7

| 28 Days | 42 Days | |
|---|---|---|
| Antibody Titers | | |
| Titer ± SE | Titer ± SE | Actual Dilution |
| $5.26 \pm 0.25$ | $9.46 \pm 0.10$ | 32,626 |

TABLE 8

| Cell-Mediated Immunity Results | | | | | |
|---|---|---|---|---|---|
| Mean Diameter ± SE | | No. Inf. | | Inf. Score | |
| 24 Hr | 48 Hr | 24 Hr | 48 Hr | 24 Hr | 48 Hr |
| $16.78 \pm 0.64$ | $12.0 \pm 0.49$ | 5/7 | 4/7 | 1.50 | 1.36 |

No significant side effects were observed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An adjuvant composition in the form of an emulsion having oily particles dispersed in a continuous aqueous phase, for potentiating the immunogenicity of an antigen, which adjuvant comprises:
   a non-toxic tetra-polyol in an emulsion-forming amount of between 0.2% and 49%;

optionally, a non-toxic metabolizable oil in an emulsion-forming amount of up to 15%;
optionally, a glycol ether-based surfactant in an emulsion-stabilizing amount of up to 5%;
water or aqueous solution; and
a muramyldipeptide derivative of formula (I):

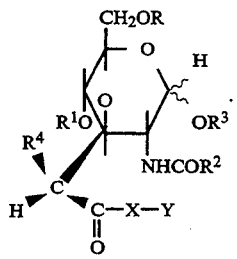

or a pharmaceutically acceptable salt thereof, wherein
R and $R_1$ are each independently H or acyl of 1 to 22 carbon atoms;
$R_2$ is alkyl or aryl, optionally substituted with halo, nitro, or lower alkyl;
$R_3$ is H, alkyl, or aryl;
$R_4$ is H or lower alkyl;
X is L-alanyl, L-α-aminobutyryl, L-arginyl, L-asparginyl, L-aspartyl, L-cysteinyl, L-glutaminyl, L-glutamyl, glycyl, L-histidyl, L-hydroxyprolyl, L-isoleucyl, L-leucyl, L-lysyl, L-methionyl, L-ornithinyl, L-phenylalanyl, L-prolyl, L-seryl, L-threonyl, L-tyrosyl, L-tryptophanyl, or L-valyl; and
Y is D-glutamine, D-isoglutamine or D-isoasparagine, in an immunopotentiating amount of between 0.0001% and 10%.

2. The adjuvant composition of claim 1 wherein said tetra-polyol has a polyoxypropylene base of molecular weight between 6500 and 7000 and has polyoxyethylene in an amount between 1% and 10% of said tetra-polyol.

3. The adjuvant composition of claim 2 which includes a non-toxic metabolizable oil, wherein said oil is squalene or squalane.

4. The adjuvant composition of claim 3 which includes a glycol ether-based surfactant, wherein said surfactant is polyoxyethylene 20 sorbitan monooleate.

5. The adjuvant composition of claim 4 wherein said water or aqueous solution comprises isotonic buffered saline.

6. The adjuvant composition of claim 5 wherein substantially all of the volume of said oily particles in said adjuvant composition is present in particles having a diameter less than about 800 nm.

7. The adjuvant of claim 6 wherein substantially all of the volume of said oily particles in said adjuvant composition is present in particles having a diameter less than about 300 nm.

8. The adjuvant composition of claim 7 wherein said muramyldipeptide derivative of formula (I) is:
N-acetylmuramyl-L-threonyl-D-isoglutamine,
N-acetylmuramyl-L-α-aminobutyryl-D-isoglutamine,
6-O-stearoyl-N-acetylmuramyl-L-α-aminobutyryl-D-isoglutamine,
N-acetylmuramyl-L-valyl-D-isoglutamine,
N-acetylmuramyl-L-alanyl-D-isoglutamine,
N-acetyl-desmethylmuramyl-L-alanyl-D-isoglutamine,
N-acetylmuramyl-L-alanyl-D-glutamine butyl ester,
N-acetylmuramyl-L-seryl-D-isoglutamine, or
N-butyrylmuramyl-L-α-aminobutyryl-D-isoglutamine.

9. The adjuvant composition of claim 8 wherein said muramyldipeptide derivative of formula (I) is N-acetylmuramyl-L-threonyl-D-isoglutamine.

10. The adjuvant composition of claim 8 wherein said muramyldipeptide derivative of formula (I) is N-acetylmuramyl-L-alanyl-D-glutamine butyl ester.

11. An adjuvant composition in the form of an emulsion having oily particles dispersed in a continuous aqueous phase, for potentiating the immunogenicity of an antigen, which adjuvant composition comprises:
a tetrapolyol in an amount of between 1% and 10%, wherein said tetrapolyol has a polyoxypropylene base of molecular weight between 6500 and 7000 and has polyoxyethylene in an amount of between 1% and 10% of said tetra-polyol;
squalane or squalene in an amount of between 1% and 10%;
polyoxyethylene 20 sorbitan monooleate in an amount of about 0.2%;
isotonic buffered saline; and
N-acetylmuramyl-L-threonyl-D-isoglutamine in an amount of between 0.0001% and 10%.

12. The adjuvant composition of claim 11 wherein substantially all of the volume of said oily particles in said adjuvant composition is present in particles having a diameter less than about 800 nm.

13. The adjuvant composition of claim 12 wherein substantially all of the volume of said oily particles in said adjuvant composition is present in particles having a diameter less than about 300 nm.

14. A process for preparing an adjuvant composition of claim 1, which process comprises:
preparing a first mixture comprising said non-toxic tetra-polyol, optionally, said non-toxic metabolizable oil, optionally said glycol ether-based surfactant, and said water or aqueous solution;
emulsifying said first mixture to produce an emulsion having oily particles dispersed in a continuous aqueous phase, wherein substantially all of the volume of said oily particles in said emulsion is present in particles having a diameter less than about 800 nm; and
combining said emulsion with said muramyldipeptide derivative of formula (I)

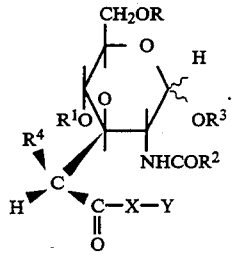

or a pharmaceutically acceptable salt thereof, wherein
R and $R_1$ are each independently H or acyl of 1 to 22 carbon atoms;
$R_2$ is alkyl or aryl, optionally substituted with halo, nitro, or lower alkyl;
$R_3$ is H, alkyl, or aryl;
$R_4$ is H or lower alkyl;

X is L-alanyl, L-α-aminobutyryl, L-arginyl, L-asparginyl, L-aspartyl, L-cysteinyl, L-glutaminyl, L-glutamyl, glycyl, L-histidyl, L-hydroxyprolyl, L-isoleucyl, L-leucyl, L-lysyl, L-methionyl, L-ornithinyl, L-phenylalanyl, L-prolyl, L-seryl, L-threonyl, L-tyrosyl, L-tryptophanyl, or L-valyl; and Y is D-glutamine, D-isoglutamine or D-isoasparagine, to form an adjuvant composition of claim 1.

15. The process of claim 14 wherein said first mixture is emulsified to obtain an emulsion wherein substantially all of the volume of said oily particles in said emulsion is present in particles having a diameter less than about 300 nm.

16. The process of claim 15 wherein said muramyldipeptide derivative of formula (I) is combined with said emulsion in the form of an aqueous solution or suspension.

17. A method for inducing an immune response in an animal having an immune system, which method comprises:

administering a vaccine comprising an immunogenic amount of an antigen; a non-toxic tetra-polyol in an emulsion-forming amount of between 0.2% and 49%; optionally, a non-toxic metabolizable oil in an emulsion-forming amount of up to 15%; optionally, a glycol ether-based surfactant in an emulsion-stabilizing amount up to 5%; water or aqueous solution; and a muramyldipeptide derivative of formula (I)

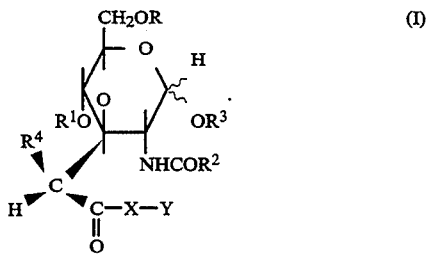

(I)

or a pharmaceutically acceptable salt thereof, wherein

R and $R_1$ are each independently H or acyl of 1 to 22 carbon atoms;

$R_2$ is alkyl or aryl, optionally substituted with halo, nitro, or lower alkyl;

$R_3$ is H, alkyl, or aryl;

$R_4$ is H or lower alkyl;

X is L-alanyl, L-α-aminobutyryl, L-arginyl, L-asparginyl, L-aspartyl, L-cysteinyl, L-glutaminyl, L-glutamyl, glycyl, L-histidyl, L-hydroxyprolyl, L-isoleucyl, L-leucyl, L-lysyl, L-methionyl, L-ornithinyl, L-phenylalanyl, L-prolyl, L-seryl, L-threonyl, L-tyrosyl, L-tryptophanyl, or L-valyl; and Y is D-glutamine, D-isoglutamine or D-isoasparagine, in an immunopotentiating amount of between 0.0001% and 10%.

18. The method of claim 17 wherein said vaccine comprises:

a tetrapolyol in an amount of between 1% and 10%, wherein said tetrapolyol has a polyoxypropylene base of molecular weight between 6500 and 7000 and has polyoxyethylene in an amount between 1% and 10% of said tetrapolyol;

squalane or squalene in an amount of between 1% and 10%;

polyoxyethylene 20 sorbitan monooleate in an amount of about 0.2%;

isotonic buffered saline;

N-acetylmuramyl-L-threonyl-D-isoglutamine in an amount of between 0.0001% and 10%; and an immunogenic amount of an antigen.

19. A vaccine for immunizing an animal, which vaccine comprises an immunogenic amount of an antigen and an adjuvant composition in the form of an emulsion having oily particles dispersed in a continuous aqueous phase, which adjuvant composition comprises:

a non-toxic tetra-polyol in an emulsion-forming amount of between 0.2% and 49%;

optionally, a non-toxic metabolizable oil in an emulsion-forming amount of up to 15%;

optionally, a glycol ether-based surfactant in an emulsion-stabilizing amount of up to 5%;

water or aqueous solution; and a muramyldipeptide derivative of formula (I)

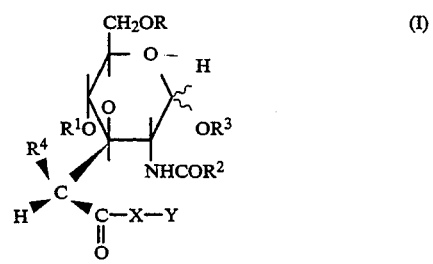

(I)

or a pharmaceutically acceptable salt thereof, wherein

R and $R_1$ are each independently H or acyl of 1 to 22 carbon atoms;

$R_2$ is alkyl or aryl, optionally substituted with halo, nitro, or lower alkyl;

$R_3$ is H, alkyl, or aryl;

$R_4$ is H or lower alkyl;

X is L-alanyl, L-α-aminobutyryl, L-arginyl, L-asparaginyl, L-aspartyl, L-cysteinyl, L-glutaminyl, L-glutamyl, glycyl, L-histidyl, L-hydroxyprolyl, L-isoleucyl, L-leucyl, L-lysyl, L-methionyl, L-ornithinyl, L-phenylalanyl, L-prolyl, L-seryl, L-threonyl, L-tyrosyl, L-tryptophanyl, or L-valyl; and Y is D-glutamine, D-isoglutamine or D-isoasparagine, in an amount of between 0.0001% and 10%.

20. The vaccine of claim 19 wherein said tetra-polyol has a polyoxypropylene base of molecular weight between 6500 and 7000 and has polyoxyethylene in an amount between 1% and 10% of said tetra-polyol.

21. The vaccine of claim 20 wherein said muramyldipeptide derivative of formula (I) is N-acetylmuramyl-L-threonyl-D-isoglutamine.

22. The vaccine of claim 20 wherein said muramyldipeptide derivative of formula (I) is N-acetylmuramyll-alanyl-D-glutamine butyl ester.

23. The vaccine of claim 21 which comprises:

a tetrapolyol in an amount of between 1% and 10%;

squalane or squalene in an amount of between 1% and 10%;

polyoxyethylene 20 sorbitan monooleate in an amount of about 0.2%;

isotonic buffered saline; and

N-acetylmuramyl-L-threonyl-D-isoglutamine in an amount of between 0.0001% and 10%.

24. The vaccine of claim 23 wherein substantially all of the volume of said oily particles in said adjuvant composition is present in particles having a diameter less than about 800 nm.

25. The vaccine of claim 24 wherein substantially all of the volume of said oily particles in said adjuvant composition is present in particles having a diameter less than about 300 nm.

26. A kit for extemporaneous preparation of an adjuvant composition, which kit comprises:

a first container containing an emulsion having oily particles dispersed in a continuous aqueous phase, where said emulsion comprises:
 a tetrapolyol which has a polyoxypropylene base of molecular weight between 6500 and 7000 and has polyoxyethylene in an amount between 1% and 10% of said tetra-polyol;
 squalane or squalene;
 polyoxyethylene 20 sorbitan monooleate;
 and isotonic buffered saline; and a second container containing an aqueous solution or suspension of N-acetylmuramyl-L-threonyl-D-isoglutamine;

where the concentrations of the components in each container are selected such that combination of the contents of both containers produces a formulation comprising said tetrapolyol in an amount of between 1% and 30%; squalane or squalene in an amount of between 1% and 30%; polyoxyethylene 20 sorbitan monooleate in an amount of between 0.2% and 5%; N-acetylmuramyl-L-threonyl-D-isoglutamine in an amount of between 0.0001% and 30%; and isotonic buffered saline.

27. A kit for extemporaneous preparation of an adjuvant composition of the invention, which kit comprises:

a first container containing an emulsion having oily particles dispersed in a continuous aqueous phase, where said emulsion comprises:
 a tetra-polyol which has a polyoxypropylene base of molecular weight between 6500 and 7000 and has polyoxyethylene in an amount between 1% and 10% of said tetra-polyol;
 squalane or squalene;
 polyoxyethylene 20 sorbitan monooleate; and
 isotonic buffered saline; and a second container containing an aqueous solution or suspension of
 N-acetylmuramyl-L-threonyl-D-isoglutamine and an immunogenic amount of an antigen;

where the concentrations of the components in each container are selected such that combination of the contents of both containers produces a formulation comprising said tetrapolyol in an amount of between 1% and 10%; squalane or squalene in an amount of between 1% and 10%; polyoxyethylene 20 sorbitan monooleate in an amount of about 0.2%; N-acetylmuramyl-L-threonyl-D-isoglutamine in an amount of between 0.0001% and 30%; an immunogenic amount of an antigen; and isotonic buffered saline.

* * * * *